United States Patent [19]

Bergstrom et al.

[11] Patent Number: 4,983,727

[45] Date of Patent: Jan. 8, 1991

[54] PALLADIUM MEDIATED REACTION OF ORGANIC DISULFIDES WITH MERCURATED NUCLEIC ACID COMPONENTS

[75] Inventors: Donald E. Bergstrom; Jeffrey A. Jenson, both of Grand Forks, N. Dak.

[73] Assignee: University of North Dakota School of Engineering & Mines Foundation, Grand Forks, N. Dak.

[21] Appl. No.: 179,751

[22] Filed: Apr. 11, 1988

[51] Int. Cl.$^5$ ............................................. C07H 19/00
[52] U.S. Cl. ...................................... 536/23; 536/120; 536/4.1
[58] Field of Search ...................... 536/23, 28, 29, 4.1, 536/120

[56] References Cited

U.S. PATENT DOCUMENTS

| | | | |
|---|---|---|---|
| 4,247,544 | 1/1981 | Bergstrom et al. | 424/180 |
| 4,267,171 | 5/1981 | Bergstrom et al. | 424/180 |
| 4,711,955 | 12/1987 | Ward et al. | 536/29 |

*Primary Examiner*—John W. Rollins
*Assistant Examiner*—James O. Wilson
*Attorney, Agent, or Firm*—Zarley, McKee, Thomte, Voorhees & Sease

[57] ABSTRACT

A method of preparing C-5 substituted nucleotides by reacting a C-5 position mercurated nucleoside with an alkyl or aryl disulfide in the presence of palladium(II) ion. The resulting new method for attaching linker arms to nucleic acids (DNA,RNA) provides a wide ranging reaction far more useful than those heretofore developed, and allows preparation of modified components with linking reactive functionality that allows usefulness as probes, therapeutics, and for DNA sequencing.

17 Claims, No Drawings

PALLADIUM MEDIATED REACTION OF ORGANIC DISULFIDES WITH MERCURATED NUCLEIC ACID COMPONENTS

BACKGROUND OF THE INVENTION

Numerous procedures employed in biomedical research and recombinant DNA technology and clinical diagnosis rely on nucleotides modified at the C-5 position for use as probes. These various utilities are based upon the ability of the molecules to be: (1) detected spectrophotometrically or (2) to form stable complexes with polypeptides which in turn can be detected, either by means of properties inherent in the polypeptide, or by means of detectable moieties which are attached to, or which interact with, the polypeptide.

Some uses include detecting and identifying nucleic acid-containing etiological agents, e.g. bacteria and viruses; screening bacteria for antibiotic resistance; diagnosing genetic disorders; and identifying tumor cells.

There are several important criteria which must be satisfied in order for a modified nucleotide to be generally suitable for use as probes in biomedical research, for clinical diagnosis and for recombinant DNA technology. The modified compound must contain a substituent or probe that is unique and not normally found associated with nucleotides or polynucleotides. The probe must react specifically with chemical or biological reagents to provide a sensitive detection system. The analogs may be relatively efficient substrates for commonly studied nucleic acid enzymes, since numerous practical applications require that the analog be enzymatically metabolized, e.g. the analogs must function as substrates for nucleic acid polymerases. For this purpose, probe moieties should not be placed on ring positions that sterically, or otherwise, interfere with the normal Watson-Crick hydrogen bonding potential of the bases. Otherwise, the substituents will yield compounds that are inactive as polymerase substrates. Normally such considerations limit substitution positions to the 5 position of a pyrimidine or pyrrolo[2,3-d]pyrimidine. Additionally, the detection system should be capable of interacting with probe substituents incorporated into both single-stranded and double-stranded polynucleotides in order to be compatible with nucleic acid hybridization methodologies. To satisfy this criteria, it is preferable that the probe moiety be attached to the pyrimidine through a chemical linkage or "linker arm" so that it can readily interface with antibodies, other detector proteins or chemical reagents.

C-5 substituted nucleosides are of seminal importance as modified components for (1) linking reactive functional group (e.g. sulfhydryl, amino, or carboxyl), biotin, fluorescent molecules, enzymes, or haptens to hybridization probe based diagnostics; (2) attaching radical generating metal complexes, crosslinking reagents, DNA cleaving reagents, and/or intercalators to sequence-specific oligonucleotides that are designed to function as therapeutic agents; and (3) linking fluorescent markers to oligonucleotides in automated DNA sequencing.

It can be seen therefore there is a real and continuing need for a convenient methodology for attaching C-5 linker arm substituents to the pyrimidine ring to allow nucleoside analogs to be prepared which will attach a variety of linker arms at the C-5 position to allow such useful compounds to be made faster, simpler, and in a more versatile manner from the standpoint of the precise linkages that may be attached at the C-5 position. Accordingly, it is a primary object of this invention to fulfill this continuing need.

Another objective of the present invention is to allow the addition of C-5 nucleoside substituents to be introduced by three different distinct strategies: First, C-5 substitution can be accomplished at the level of simple nucleosides in order to construct simple monomeric building blocks suitable for use in automated DNA synthesizers; secondly, modified nucleoside triphosphates can be constructed that will participate in enzyme reactions (DNA and RNA polymerases) that yield nucleic acids with the modification incorporated; and thirdly, DNA or RNA can be used as a probe by directly modifying via mercuration followed by a second reaction to attach the C-5 linker arm to the nucleic acid.

The manner of accomplishing each of the above objectives as well as others will become apparent from the detailed description of the invention which follows hereinafter.

SUMMARY OF THE INVENTION

A new method for attaching linker arms to the C-5 position of nucleosides, and nucleotides as well, to prepare C-5 substituted pyrimidine nucleoside analogs. The method involves a new chemical reaction between C-5 mercurated nucleosides and organic disulfides resulting in a thio-ether linkage to the nucleoside. The reaction requires no protective groups, has no problems with regio-selectivity and easily goes under mild conditions.

DETAILED DESCRIPTION OF THE INVENTION

While the hereinafter description of this invention is given from the standpoint of attaching linker arms to nucleic acids, it should be understood that the technology is completely applicable at three levels of complexity, i.e. it can be used for nucleosides; it can be used for nucleoside triphosphates; and it can be used with oligonucleotides.

In word form, the reaction involves reacting a C-5 position mercurated nucleoside with an alkyl or aryl disulfide in the presence of palladium(II) ion to provide a direct simple addition reaction at the C-5 position of the nucleoside. The reaction can be summarized by the following equation:

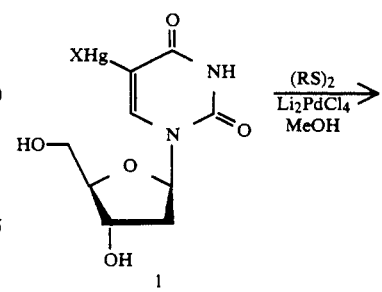

-continued

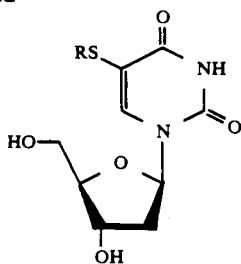

In the above identified reaction X represents any suitable anion, and it may be an organic anion such as a mercury carboxylate, an acetate, propionate, etc., or it may be an inorganic anion such as sulfate, phosphate, or a halide such as chloride, iodide, bromide, etc. The starting C-5 position mercurated nucleoside can be initially synthesized, or purchased from supply houses. C-5 mercurated nucleosides can be synthesized by the method of Bergstrom and Ruth, *J. Carbohydrates-Nucleosides-Nucleotides*, 1977, 4, 257, and Bergstrom and Schweickert, *J. Carbohydrates-Nucleosides, Nucleotides*, 1978, 5, 285–296. C-5 mercurated nucleoside mono-, di-, and triphosphates can be synthesized according to procedures published, Dale et al, *Proc. Nat. Acad. Sci. U.S.A.*, 70, 2238 (1973); and Dale et al, *Biochem.*, 1975, 14, 2458. The mercurated nucleotide can also be purchased commercially from companies such as Sigma Chemical Company, Pharmacia, Inc. or U.S. Biochemical Corp. Mercurated polynucleotides can also be synthesized in accordance with the reactions disclosed in a series of Hopman et al. articles: Hopman, A. H. N.; Wiegert, J.; Tesser, G. I.; van Duijn, P.; "A non-radioactive in situ hybridization method based on mercurated nucleic acid probes and sulfyhydryl-hapten ligands"; *Nucleic Acids Research*, 1986, 14, 6471–6488; Hopman, A. H. N.; Wiegert, J.; van Duijn, P.; "A new hybridocytochemical method based on mercurated nucleic acid probes and sulfhydryl-hapten ligands. I. Stability of the mercury-sulfhydryl bond and influence of the ligand structure on immunochemical detection of the hapten"; *Histochemistry* 1986, 84, 169–178; and Hopman, A. H. N.: Wiegert, J.; van Duijn, P.; "A new hybridocytochemical method based on mercurated nucleic acid probes and sulfhydryl-hapten ligands. II. Effects of variations in ligand structure on the in situ detection of mercurated probes"; *Histochemistry*, 1986, 85, 1–4.

The disulfide ($RS_2$) can be any desired alkyl or aryl disulfide and is in reality not a limiting factor of the invention. In fact, it is the versatility of the alkyl or aryl disulfide that can be used which makes the reaction especially attractive in that a variety of linker arms can be attached at the C-5 position of the nucleoside. Perhaps the only realistic limits are that the disulfide must be free of any unprotected amine or hydroxyl group in the beta position. Preferably it is an alkyl sulfide, however, and that the alkyl be from $C_1$ to $C_{10}$. However, straight or branched or substituted chain alkyl groups may be used, and R can by aryl, alkylaryl, alkoxyalkyl, or the like, preferably of $C_1$ to $C_{20}$ carbons. Preferably R is a substituted alkyl, substituted with a functional group useful for cross-linking such as a tertiary amine, protected primary or secondary amine, ether, amide, carboxy, alkoxycarbonyl, carbonyl halide, or complex moieties such as biotin, substituted acridines, haptens, or metal chelating ligands The reaction times are straightforward and non-critical, and vary from a few hours to overnight, depending upon the value of "R." It is preferred that the reaction be run at about room temperature up to about 65° C. The amount of disulfide should be from equimolar up to about an 8 fold excess.

As can be seen, the reaction is run in the presence of a source of palladium(II) ion. The amount of palladium(II) varies from equimolar up to about a two-fold excess.

The reaction source of palladium(II) ion is not critical. Most preferably it is a salt like palladium chloride. It is preferred that the reaction is conducted in the presence of lithium chloride, in which case the reaction ingredient is often referred to as dilithium tetrachloropalladate having the formula: $Li_2PdCl_4$.

In particular, the reaction with the C-5 mercurial nucleoside is conducted in the presence of a palladium salt such as lithium trichloropalladite ($LiPdCl_3$) or dilithium tetrachloropalladate ($Li_2PdCl_4$) with the result being transmetallation by the lithium palladium salt and addition of the resulting organopalladium intermediate to the C-5 position followed by rearrangement.

The palladium salt source of palladium(II) ion may be, for example, $LiPdCl_3$, $Li_2PdCl_4$, $PdCl_2$, $PdCl_2$ coordinated with acetonitrile or benzonitrile, $Pd(OAc)_2$, or $Pd(O_2CCF_3)_2$, $Pd(NO_3)_2$.

The palladium(II) sources employed in forming the C-5 substituted nucleosides according to the synthesis of this invention may be palladium(II) salts of any of the conventional anions. They include the halides, such as chloride, bromide, and iodide, sulfate, nitrate, acetate, trifluoroacetate, phosphate, propionate, and others known to those skilled in the art. In summary, the precise anion of the palladium salt employed is not critical.

It should be noted that the reaction is described as a palladium(II) mediated reaction. The reaction is not a catalytic reaction, but involves palladium mediation followed by rearrangement. Preferably, the source of palladium(II) is lithium palladium chloride or palladium acetate.

The reaction as depicted is shown as being conducted in methyl alcohol. Other alcohols and like organic solvents could also be used. Solvent medium is not critical and the reaction may be able to be conducted in an aqueous medium as well. For ease of simplicity, methanol medium is preferred.

It is, of course, possible that the disulfides themselves can be linked to other useful functional groups to provide even more versatile linker arms. For example, the palladium mediated coupling reaction of disulfide may include disulfides which include as part of their structure a spacer linked to an activated ester, amine, biotin, fluorophore, hapten or enzyme.

In earlier describing the invention, it has been described with regard to mercuration of 2'-deoxyuridine. However, as those skilled in the art know, the 2'-deoxyuridine may be modified, or perhaps a better word is substituted, both in the sugar residue by other sugars and in the base residue by other bases. For example, looking first at the sugar residue, that is the 2'-deoxyribose may be replaced with 2',3'-dideoxyribose, ribose itself or arabinose. The uracil base moiety may be replaced by cytosine, 7-deazaadenine, or 7-deazaguanine. Also, the sugars may be phosphorylated as well. In sum, the compound which is C-5 mercurated may be described as a substituted nucleic moieties and their analogs. The various moieties which may be used, both with regard to the pyrimidines and the 7-deazapurines, sometimes referred to as pyrrolo[2,3 d]-pyrimidines, may be represented as follows:

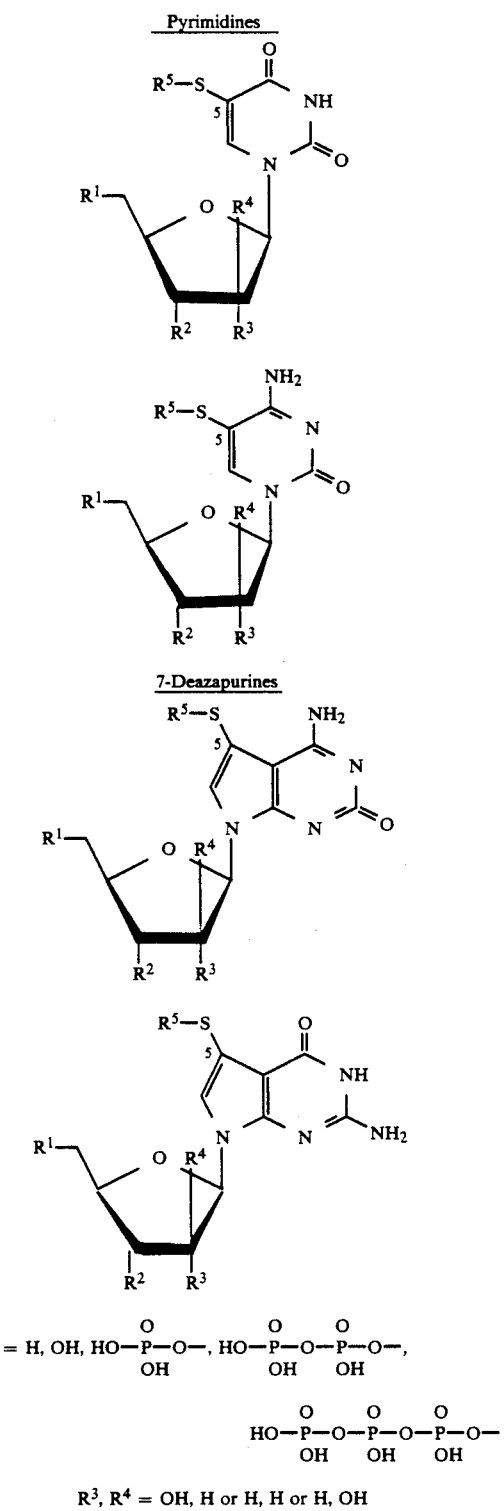

$R^1, R^2 =$ H, OH, HO—P(=O)(OH)—O—, HO—P(=O)(OH)—O—P(=O)(OH)—O—,

HO—P(=O)(OH)—O—P(=O)(OH)—O—P(=O)(OH)—O—

$R^3, R^4 =$ OH, H or H, H or H, OH $R^1$ and $R^2$ also represent the 5' and 3' ends of oligodeoxyribo- and oligoribonucleotide chains into which the above nucleoside units are incorporated.

As earlier indicated, the C-5 substituted nucleosides, nucleotides, and oligonucleotides prepared in accordance with this invention are useful as probes, for use in therapeutics, and for use in oligonucleotide sequencing.

The modified C-5 polynucleotides of this invention are capable of denaturization and renaturization under conditions compatible with their use as hybridization probes. They, therefore, can be used as probes for detecting and/or localizing specific polynucleotide sequences in filter hybridization assays or in chromosomes, fixed cells, or tissue sections. This general scheme can also be used equally well for the detection of nucleic acid sequences of bacterial, viral, fungal or parasite or in clinical samples, and thus these C-5 modified nucleotides form the basis of a powerful new approach to clinical diagnostics which does not rely upon the use of radioisotopes. It therefore can be seen that the basic reaction of the present invention is of tremendous potential importance.

The C-5 modified polynucleotides prepared in accordance with this invention, as earlier stated, do not interfere with the normal hydrogen bonding and complementary base pairing in the Watson-Crick model. Thus, these modified polynucleotides may be used to probe for any desired nucleotide sequence. The polynucleotide may, for example, be hybridized with nucleic acids obtained from an organism under scrutiny. Hybridization indicates complementary base pairing, and the hybridized nucleic acid duplexes are identified by forming a complex between the duplex and a suitable polypeptide (e.q. strepavidin, antibody, or enzyme) which recognizes and selectively binds to the group linked through C-5 on the modified oligonucleotide. Positive detection of the moiety indicates that the complex, the duplex, and therefore the nucleic acid sequences of interest are present.

This approach can be extended to diagnosis of genetic disorders as well. Thus, the deoxyribonucleic acid gene sequence whose presence or absence is associated with a particular disorder can be detected following hybridization with a C-5 modified polynucleotide probe according to this invention based upon complex formation with suitable detectable polypeptides.

The palladium medicted coupling reaction will also provide a means to tether intercalating agents, such as acridine or methidium dyes, alkylating agents, metal ligands designed to mediate DNA cleavage, or enzymes to oligonucleotides designed to function as sequence-specific nucleases and/or therapeutic agents. The concept of these analogs as therapeutic agent has been discussed at the National Cancer Institute/National Institute of Allergy and Infectious Diseases (NIC/NIAID) Workshop on Anti-Sense Oligonucleotide as Therapeutic Agents, held in Annapolis, Md., Sept. 13-15, 1987, and sponsored by the Developmental Therapeutics Program, Division of Cancer Treatment, National Cancer Institute, and the National Institute of Allergy and Infectious Diseases.

The use of these substances as tools for molecular biology research involving sequence-specific cleavage of nucleic acids has been reviewed by H. E. Moser et al., Science, 1987, 238, 645-650.

Finally, C-5 substituted pyrimidine nucleoside triphosphates can be used in DNA sequencing via enzymic incorporation and chain termination as discussed by Proben et al., *Science*, 1987, 238, 336–341.

The following examples are offered to further illustrate but not limit the process of this invention.

EXAMPLE $^1$H and $^{13}$C NMR were recorded on a Varian VXR 300 Spectrophotometer in d4-MeOH with tetramethylsilane as the internal standard. Elemental analyses were performed by Galbraith Laboratories, Inc., Knoxville, Tenn. Palladium chloride was obtained from Matthey Bishop. The 0.1M solution of Li$_2$PdCl$_4$ in methanol was made by stirring a suspension of one equivalent of PdCl$_2$ and two equivalents of dry LiCl in the appropriate amount of methanol overnight. Column chromatography was done on E. M. Science Kieselgel 60 (70–230 mesh). Analytical thin layer chromatography was carried out on E. Merck precoated silica gel F-254 (0.25 mm) plastic backed TLC sheets cut to 35×110 mm. Elution was with MeOH/CHCl$_3$ (15:85 v/v). For reference 2'-deoxyuridine has an R$_f$ of 0.29. All solvents and reagents were reagent grade.

5-(Chloromercuri)-2'-deoxyuridine (0.926 g, 2.0 mmol), the disulfide (5 mmol) and a 0.1M solution of Li$_2$PdCl$_4$ in methanol (40 mL) were stirred at ambient temperature for 14–16 hours. The reaction was then worked up by treating the solution with either H$_2$S for thirty seconds or by adding NaBH$_4$ until precipitation of black mercury/palladium was complete. With some disulfide reactions the H$_2$S or NaBH$_4$ treatment is unnecessary and the concentrate crude reaction mixture can be directly applied to silica gel. In this example the solution obtained on gravity filtration was evaporated in vacuuo to give an oil that was purified on a silica gel column eluting with a linear chloroform/methanol gradient that varied from 0 to 50% methanol. Fractions containing the product were combined and evaporated to obtain the pure product.

EXAMPLES 2–6

The process generally repeated in Example 1 was repeated wherein R=—(CH—$_2$)$_3$CH$_3$, —C$_6$H$_5$, —CH$_2$CH$_2$CO$_2$CH$_3$, —CH$_2$CH$_2$CO$_2$H, and —CH$_2$CH$_2$NHCCF$_3$.

It can be seen that the process herein defined provides a novel reaction for attaching at the C-5 position linker arms to pyrimidine-containing nucleosides for use as probes, for use in therapeutics, and for use in oligonucleotide sequencing. None of the attachments at the C-5 position evidence interference with the normal Watson-Crick hydrogen bonding, complementary base-pairing process.

What is claimed is:

1. A process of preparing a C-5 substituted nucleoside useful as linking units for probes, therapeutics and nucleotide sequencing, said process comprising:

reacting a C-5 mecuri-substituted nucleic acid moiety of the formula:

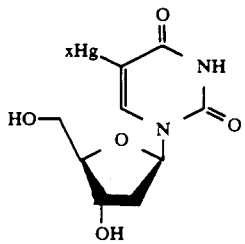

wherein X is a soluble organic or inorganic ion, with a disulfide of the formula (RS)$_2$,
wherein R is a C$_1$ to C$_{20}$ alkyl, aryl, alkylaryl, alkoxyalkyl, alkyl carboxyl, aklylcarboxamido, alkyl carbonyl or a C$_1$ to C$_{20}$ functionally substituted alkyl group,
said reaction occurring in the presence of a mediating effective amount of palladium(II) ion source to provide a C-5 substituted nucleoside having a C-5 linker arm attached which will not interfere with the normal Watson-Crick hydrogen bonding process.

2. The process of claim 1 wherein X is an organic ion.

3. The process of claim 1 wherein X is an inorganic ion.

4. The process of claim 3 wherein X is a halide ion.

5. The process of claim 2 wherein R is a functionally substituted alkyl group.

6. The process of claim 2 wherein R is a C$_1$ to C$_{10}$ alkyl.

7. The process of claim 1 wherein the palladium(II) ion source is a palladium(II) salt.

8. The process of claim 7 wherein the source of palladium(II) is dilithium tetrachloro palladate.

9. The process of claim 1 wherein said reaction is conducted using an excess of alkyl disulfide over the equimolar stoichiometric amounts.

10. The process of claim 1 wherein said reaction is conducted in the presence of an organic solvent.

11. The process of claim 1 wherein said reaction is conducted in an aqueous medium.

12. The process of claim 1 wherein the C-5 substituent is a fluorescent marker.

13. The process of claim 1 wherein said C-5 substituent is biotin.

14. The process of claim 1 wherein C-5 substituent is a hapten.

15. The process of claim 1 wherein said reaction is conducted at a temperature within the range of from 0° C. up to about 65° C.

16. The process of claim 10 wherein said solvent is methanol.

17. The process off claim 1 wherein R is a C$_1$ to C$_{10}$ functional substituted alkyl group.

* * * * *